United States Patent [19]

Polak et al.

[11] Patent Number: 4,824,528

[45] Date of Patent: * Apr. 25, 1989

[54] GAS DETECTION APPARATUS AND METHOD WITH NOVEL ELECTROLYTE MEMBRANE

[75] Inventors: Anthony J. Polak, Lake Zurich; Sandra Petty-Weeks, Naperville, both of Ill.

[73] Assignee: Allied-Signal Inc., Morristown, N.J.

[*] Notice: The portion of the term of this patent subsequent to Apr. 28, 2004 has been disclaimed.

[21] Appl. No.: 70,650

[22] Filed: Jul. 6, 1987

Related U.S. Application Data

[63] Continuation of Ser. No. 756,614, Jul. 19, 1985, abandoned, which is a continuation-in-part of Ser. No. 687,348, Dec. 28, 1984, abandoned.

[51] Int. Cl.$^4$ ............................................. G01N 27/58
[52] U.S. Cl. ...................................... 204/1 T; 204/424; 204/426; 204/427
[58] Field of Search ............... 204/1 T, 1 P, 1 S, 1 H, 204/400, 421, 424, 425, 426, 427, 428; 73/19; 429/30, 33, 192

[56] References Cited

U.S. PATENT DOCUMENTS

| | | | |
|---|---|---|---|
| Re. 28,792 | 4/1976 | Ruka et al. .................... 204/427 X |
| 2,882,329 | 4/1959 | Liebhafsky .................... 204/421 X |
| 3,134,697 | 5/1964 | Niedrack .......................... 429/30 |
| 3,265,536 | 8/1966 | Miller et al. ........................ 204/296 |
| 3,276,910 | 10/1966 | Grasselli et al. ...................... 136/86 |
| 3,342,558 | 9/1967 | Reinecke ...................... 204/421 X |
| 3,407,249 | 10/1968 | Landi ............................ 204/296 X |
| 3,576,730 | 4/1971 | Spacil ........................... 204/427 X |
| 3,871,981 | 3/1975 | Flais et al. ..................... 204/427 X |
| 4,024,036 | 5/1977 | Nakamura et al. ................. 204/129 |
| 4,025,412 | 5/1977 | Laconti ......................... 204/427 X |
| 4,040,929 | 8/1977 | Bauer et al. ........................ 204/427 |
| 4,083,765 | 4/1978 | Lawson .............................. 204/427 |
| 4,167,457 | 9/1979 | Giner .................................. 204/1 T |
| 4,171,253 | 10/1979 | Nolan et al. ..................... 204/1 T X |
| 4,179,491 | 12/1979 | Howe et al. .......................... 423/253 |
| 4,227,984 | 10/1980 | Dempsey et al. ............... 204/424 X |
| 4,306,774 | 12/1981 | Nicholson .......................... 350/337 |
| 4,324,760 | 4/1982 | Harris ................................... 422/98 |
| 4,324,761 | 4/1982 | Harris ................................... 422/98 |
| 4,373,375 | 2/1983 | Terhune et al. ........................ 73/19 |
| 4,661,211 | 4/1987 | Petty-Weeks .................... 204/427 X |

OTHER PUBLICATIONS

J. S. Lundsgaard et al., "A Novel Hydrogen Gas Sensor: Based on Hydrogen Uranyl Phosphate", Solid State Ionics 7 (1982), 53–56.

"Hydrogen Detector Uses Silver-Palladium Probe", Platinum Metals Review, Johnson Matthey Public Limited Co., Hatton Garden, London, vol. 27, No. 1, Jan. (1983), p. 8.

T. N. Marshall, "A Thin-Film Hydrogen Sensor", p. 29, Instrumentation, Technology, 8/1972.

Hackh's Chemical Dictionary, Fourth Edition, McGraw-Hill Book Co., p. 431.

The Condensed Chemical Dictionary, Ninth Edition, Van Nostrand Reinhold Co., p. 583.

Primary Examiner—Nam X. Nguyen
Attorney, Agent, or Firm—Thomas K. McBride; Harold N. Wells

[57] ABSTRACT

Apparatus and method for detecting and measuring hydrogen and gaseous compounds capable of dissociating into or combining with hydrogen ions using a solid electrolyte concentration cell. A novel solid electrolyte membrane is used which comprises an organic polymer-inorganic compound blend prepared by admixing an organic polymer such as poly(vinyl alcohol) with a phosphoric acid in a mutually miscible solvent. A reference gas or a solid reference substance is used. For increased strength, a membrane may be composited with or attached to a porous support.

20 Claims, 3 Drawing Sheets

GAS DETECTION APPARATUS AND METHOD WITH NOVEL ELECTROLYTE MEMBRANE

CROSS-REFERENCE TO RELATED APPLICATION

This is a continuation application of pending application Ser. No. 756,614, filed on July 19, 1985, which is a continuation-in-part of application Ser. No. 687,348, filed Dec. 28, 1984 all abandoned.

FIELD OF THE INVENTION

This invention relates to electrochemical measurement and detection. More specifically, it relates to the use of a novel solid electrolyte and a catalyst in detecting the presence of hydrogen or gases capable of dissociating to yield or combine with hydrogen ions, including oxygen, and measuring the quantity present. The solid electrolyte may be formed by blending an inorganic compound and an organic polymer or by compositing a membrane comprising these components with a porous support. This invention also involves the use of a reference substance in solid form in place of a reference substance in gaseous form.

INFORMATION DISCLOSURE

U.S. Pat. No. 4,024,036 (Nakamura et al.) describes a proton permselective solid state member capable of exhibiting ionic conductivity.

U.S. Pat. Nos. 3,256,536 (Miller et al.), 4.306,774 (Nicholson), 3,276,910 (Grasselli et al.), and 4,179,491 (Howe et al.) deal with substances capable of conducting hydrogen ions.

An article by Lundsgaard et al. (Solid State Ionics 7, 1982, North-Holland Publishing Co.) describes experiments done using a substance which conducts hydrogen ions.

A hydrogen detector using more complex methods than that of the invention may be seen in U.S. Pat. No. 4,373,375 (Terhune et al.) and on p. 8 of *Platinum Metals Review*, January 1983, produced by Johnson Matthey, London. Three references showing hydrogen detectors which use an entirely different principle than the present invention are U.S. Pat. Nos. 4,324,760 and 4,324,761 (Harris) and an article on p. 29 of the August, 1972, *Instrumentation Technology*.

U.S. Pat. No. 4,040,929 (Bauer et al.) shows the use of a solid reference in an oxygen sensor.

BRIEF SUMMARY OF THE INVENTION

The present invention provides methods and apparatus for detecting gaseous hydrogen, hydrogen ion, dissociable hydrogen compounds, and compounds capable of combining with hydrogen ion, in order to indicate the presence or absence of these substances and, where desired, provide quantitative information on the amount present.

A novel solid electrolyte membrane is used in the present invention. I have discovered that a macroscopically homogeneous thin film polymer-blend membrane may be fabricated by admixing sulfuric acid or a phosphoric acid with an organic polymer which is at least partially compatible with said acid to form a polymer-blended composition of matter which is useful in gas detection. This membrane is capable of acting as a proton conductor in a hydrogen detector where molecular hydrogen is converted into protons on one side of the membrane, protons are then transported through the membrane, and protons are recombined with electrons to form molecular hydrogen on the other side. The membrane is also useful in detection of gases capable of dissociating into or combining with hydrogen ions.

In addition, the composition of matter utilized for said membrane may be composited on a porous support to form a composite membrane which possesses increased strength as well as being a protonic conductor. Examples of material used for such porous support include glass cloth, polysulfone, and ceramics.

The invention utilizes a concentration cell whose electrolyte is said membrane or composite membrane. A membrane is mounted in a sample cell or membrane housing having a sample gas chamber and a reference chamber, which chambers are separated by a partition comprising the membrane. The sample gas chamber contains the gas sample of interest, which must include a component capable of dissociating to form hydrogen ions or capable of combining with hydrogen ions. In the other chamber is a reference gas whose composition is known or a solid reference substance which exhibits a substantially constant known hydrogen partial pressure during use of the inventiion. Molecular transport through the membrane must be sufficiently slow so that gases will not mix by diffusing through it.

A catalytic agent for promotion of dissociation or combination is in intimate contact with the membrane on the sample gas side. Catalytic agent is also provided in a like manner on the side. It is not necessary that the same catalytic agent be used on both sides. Means for forming electrical contact and transferring electrons to and from an external circuit are provided on each side of the electrolyte in intimate contact with catalytic agent. The cell EMF is measured across said means for forming electrical contact and provides an indication of the presence of hydrogen or gaseous capable of combining with it in the sample gas and/or a quantitative measure of the amount of such which is present.

The method of the invention may be summarized as a method for detection, in a gas sample, of a gaseous component which is capable, in the presence of a catalytic agent, of dissociating to yield hydrogen ions or of combining with hydrogen ions, such method comprising contacting said gas sample with a first surface of a thin film polymer-blend membrane and detecting EMF between means for forming electrical connection with two separate portions of a catalytic agent effective to promote dissociation and combination, where a first portion of catalytic agent is in contact with said first surface and a second portion of catalytic agent is in contact with a second surface of said membrane, which membrane isolates said gas sample from a reference substance and has said second surface exposed to the reference gas, said membrane comprising a blend of a compound selected from the group consisting of phosphoric acids and sulfuric acid and a polymer which is compatible with said compound.

A calculating device may be used to automatically calculate concentrations, or calculation may be accomplished manually. This device may receive input from a temperature probe, or temperature may be entered manually for use in the calculation. Temperature of the gas or gases and/or the membrane housing may be controlled at a pre-established value. The catalytic agent may be platinum, palladium, or alloys thereof. The catalytic agent may be electrically conductive. Where temperature of the sample gas is too high or low for effective detection, it may be adjusted before the gas is contacted with the electrolyte element. It may be necessary to adjust the concentration, in a known manner, of sample gas contacting the membrane in order to achieve effective detection.

BACKGROUND OF THE INVENTION

Figure 1:
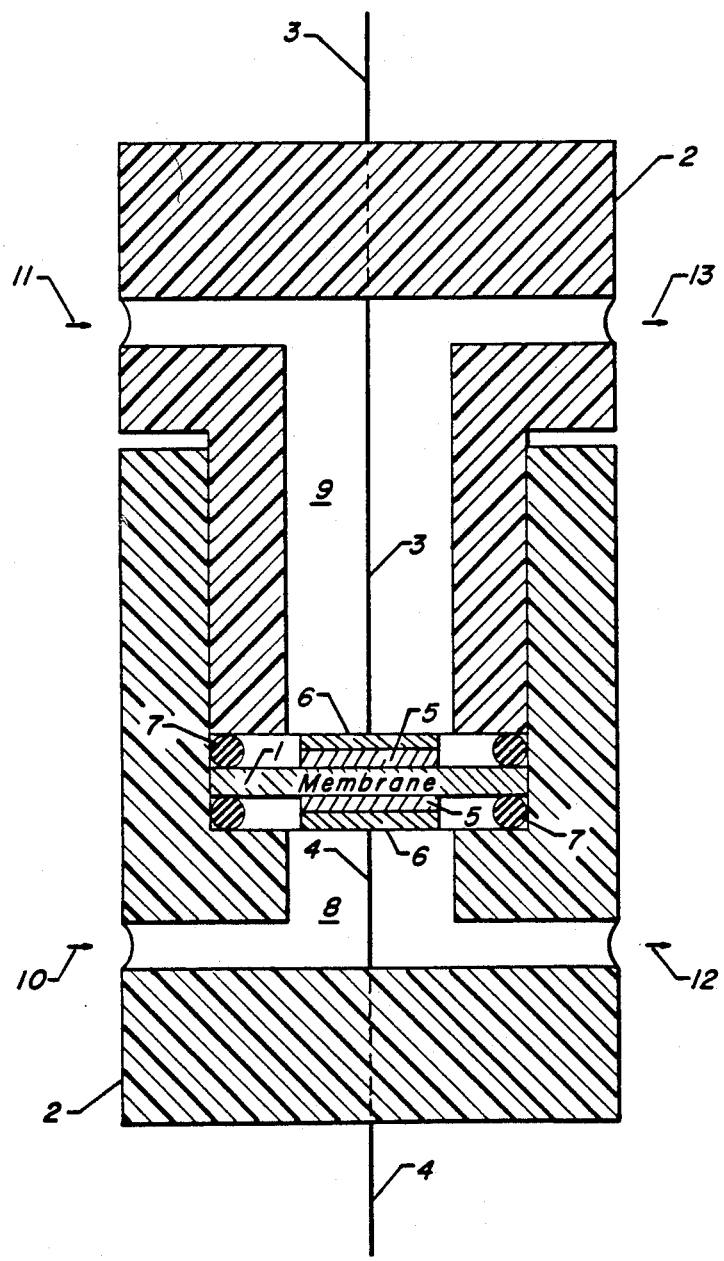
FIG. 1 is a schematic representation, in cross-section, of a test sensor used in initial proof of principle experimentation. The drawing is not to scale.

The present invention utilizes a solid electrolyte sensor for detection of certain gases. The Nernst equation describes the behavior of sensing devices using solid electrolytes. When two media with different partial pressures, $P_1$ and $P_2$, of a particular substance present in both media are separated by a solid electrolyte (ionic conductor) and conducting electrodes are attached to both sides of the ionic conductor, an EMF is generated which is related to the partial pressures as follows:

$$EMF = E_o + (RT/nF)ln(P_2/P_1),$$

where R is the gas constant, T is absolute temperature, F is the Faraday constant, $E_o$ is the standard oxidation-reduction potential difference, EMF is electromotive force, and n is the number of electrons per molecule of product from the overall cell reaction.

If the system described by the above equation behaves nonideally, the partial pressures must be replaced by fugacities. Another factor which may need to be considered in regard to a particular system is the rate of dissociation to form the ions which pass through the solid electrolyte. This may be a limiting factor to the transfer of ions through the electrolyte. The rate of dissociation can be calculated by means of the equilibrium constant for the dissociation reaction.

The magnitude of EMF produced is generally in accordance with the parameters discussed herein: the Nernst equation and, where applicable, the dissociation equilibrium constant. However, required practice in measuring concentration is to periodically calibrate the measuring apparatus by use of samples whose composition is known. Thus, exact adherence to theoretical relationships is not required of commercially used methods and apparatus. The primary commercial requirement is repeatability.

In a majority of cases, the admixture of an organic compound, especially in a polymeric state, with an inorganic compound, results in a phase separation, due to the fact that the two systems are immiscible in nature. However, we have discovered that a macroscopically homogeneous thin film polymer-blend membrane may be fabricated by admixing the organic and inorganic components discussed herein; the resulting substance is not merely a physical mixture but exhibits a degree of interaction, that is, some amount of chemical interaction exists. Substances which are permeable by gases in a selective manner are known and utilized in a variety of applications. A membrane formed in accordance with the present disclosure is substantially impermeable to ions and gases, including hydrogen gas, but does allow hydrogen ions to pass through it. For background information relating to the principles of the present invention, reference may be made to the book *Solid Electrolytes and Their Applications*, edited by Subbarao, Plenum Press, 1980.

Low mechanical strength has been a common problem when attempting to apply permselective membranes. The present invention provides a membrane whose mechanical strength is increased by compositing it with other materials, but whose desirable properties are not lost as a result of doing so.

Also used in the present invention is a solid substance which is a substitute for a reference gas, which reference gas is one of the two media mentioned above in the discussion of the Nernst equation. It is highly desirable to use a solid reference substance, which requires only periodic replacement, instead of maintaining a continuous reference gas flow, or in appropriate situations, maintaining a sealed chamber of reference gas. The reference substance is in intimate contact with the catalytic agent on the reference side of the membrane. One substance may serve as both reference substance and catalytic agent.

DETAILED DESCRIPTION OF THE INVENTION

As was mentioned above, in attempting to blend an organic polymer with an organic compound, the usual result is to obtain a phase separation. It has now been discovered that a useful blend may be obtained by admixing certain organic polymeric compounds with sulfuric acid or a phosphoric acid. The resulting composition of matter is formed into a thin film membrane which may be utilized in gas detection systems. The utility of these membranes in gas detection devices is due to the fact that the membranes possess a high protonic conductivity, especially at room or ambient temperature.

Usually, high conductivity is observed in polymer complexes only when the temperature is above the glass transition temperature (Tg), that is, above the temperature at which the substance changes from a solid to a liquid (the melting point of a polymer is usually above its glass transition temperature). Indications of the change of a polymer from solid to liquid are abrupt changes in certain properties, such as coefficient of expansion and heat capacity. The polymer-blend compositions of the present invention exhibit high protonic conductivity at temperatures well below the observed glass transition temperatures of the individual homopolymers. A device utilizing an ion-conducting polymer must operate below the Tg of the polymer; the polymer is not usable at higher temperatures due to loss of strength, tackiness, etc. A polymer-blend of the present invention will exhibit two second order transition temperatures, which are attributable to the individual components. Note that the glass transition is a second order transition. A transition associated with a polymer in a blend of the present invention will occur at a different value than the transition temperature determined for that polymer when it is not mixed with any other substance. The transition temperature associated with the inorganic component depends on the polymer component in the blend. Thus, it may be appreciated that there is a degree of interaction between the components, that is, at least some chemical interaction exists between the components.

A distinct advantage which is possessed by the polymer-blend membranes of the present invention over other organic-inorganic blend membranes is that these membranes possess low resistivities (resistance times area divided by thickness), which are four to five orders of magnitude less than the other organic-inorganic blends. In using a gas sensor of the type of the present invention, it is necessary to measure the output voltage. When utilizing a membrane of the instant invention, it will be possible to use a voltage measuring device of lower impedance. Use of such a device will result in a simplified and lower cost electronics package for a commercial hydrogen sensor. A voltmeter should have an impedance (AC resistance) at least 3 orders of magnitude greater than that of the system in which it is used for measurement; high impedance voltage measuring devices are more costly than those of low impedance. In addition, a device with reduced impedance is less sensitive to electromagnetic interference than a high impedance device. This permits the device to be located in an electrically noisy environment without adversely affecting its performance.

The desired membrane comprises a blend of an organic polymer and a phosphoric acid or sulfuric acid, the polymer being at least partially compatible with the acid. Examples of organic polymers which may be employed as one component of the blend of the present invention will include poly(vinyl alcohol), also known is PVA, poly(vinyl fluoride), polyethylenimine, poly(acrylic acid), polyethylene glycol, cellulose acetate, phenol formaldehyde resins, poly(vinyl pyrrolidone), poly(ethyloxazoline), poly(acrylamide), poly(N-isopropyl acrylamide), poly(N,N-dimethyl acrylamide), poly(vinyl 4-pyridine), polyimide, poly(vinyl sulfonic acid), etc. Further examples of organic polymers which may be employed include copolymers having monomer units of these exemplary polymers. In terms of monomer repeat units, the polymer-blend membrane comprises a polymer selected from a group of polymers made from 2-ethyl-2 oxazoline or a polymer or copolymer having repeat units selected from a group comprising hydroxyethylene, vinyl fluoride, ethyleneimine, acrylic acid, ethylene glycol, cellulose acetate, acrylamide, N-isopropyl acrylamide, N,N-dimethyl acrylamide, 4-pyridylethylene, imide, vinyl sulfonic acid, N-pyrrolidonylethylene, and polyphenolic structures such as phenol formaldehyde resins.

The other component of the organic-inorganic blend will comprise a phosphoric acid or sulfuric acid. Examples of acids which may be employed will include hypophosphoric acid, metaphosphoric acid, orthophosphoric acid, pyrophosphoric acid, polyphosphoric acid, or sulfuric acid. The sulfuric acid which is employed will comprise an aqueous sulfonic acid which may contain from about 10% to about 40% sulfuric acid in aqueous solution. It is to be understood that the aforementioned organic polymers and phosphoric acids or sulfuric acid are only representative of the class of components which make up the membrane blends used in the present invention.

The novel compositions of matter used in the present invention are prepared by admixing the two components of the blend in a mutually miscible solvent at solution conditions for a period of time sufficient to form the desired blend. In the preferred membrane the mutually miscible solvent which is employed to dissolve the components comprises water, although it is contemplated within the scope of this application that any other mutually miscible solvent, either inorganic or organic in nature may also be employed. The mixing of the two components of the composition of matter may be effected at solution conditions which will include a temperature in the range of from about ambient (20°-25° C.) up to the boiling point of the mutually miscible solvent which, for example, in the case of water is 100° C. As an example, poly(vinyl alcohol) and orthophosphoric acid may be placed in a flask and dissolved in water which has been heated to 100° C. The blend is cast upon a suitable casting surface which may consist of any suitable material sufficiently smooth in nature so as to provide a surface free of any defects which may cause imperfections on the surface of the membrane. Examples of suitable casting surfaces may include metals such as stainless steel, aluminum, etc., glass, polymer or ceramics. After casting the solution upon the surface, the solvent is then removed by any conventional means including natural evaporation or forced evaporation by the application of elevated temperatures whereby said solvent is evaporated and the desired membrane comprising a thin film of the polymer blend is formed. The thickness of the film can be controlled by the amount of phosphoric or sulfuric acid and/or polymer which is present in the reaction mixture or by the depth of the casting vessel. The thin film organic-inorganic blend which is prepared according to the process of the present invention will possess a thickness which may range from about 0.1 to over 500 microns and preferably from about 20 to about 60 microns.

The amounts of phosphoric or sulfuric acid and organic polymer used in the blend may vary over a relatively wide range. For example, the acid may be present in the blend in a range of from about 1% to about 70% by weight of the blend while the organic polymer may be present in an amount in the range of from about 99% to about 30% by weight of the blend. Preferably, the acid is present in the blend in an amount of from about 37 to 70% by weight and the polymer is present in the blend in an amount of from about 63 to 30% by weight. Whenever a composition is expressed herein, it is to be understood that it is based, in the case of polymers, on the monomer repeat unit.

Examples of novel thin film polymer blends which may be prepared according to the process of this invention will include poly(vinyl alcohol)-orthophosphoric acid, poly(vinyl fluoride)-orthophosphoric acid, cellulose acetate-orthophosphoric acid, polyethylene glycol-orthophosphoric acid, poly(vinyl alcohol)-pyrophosphoric acid, poly(vinyl fluoride)-pyrophosphoric acid, cellulose acetate-pyrophosphoric acid, polyethylene glycol-pyrophosphoric acid, poly(vinyl alcohol)-metaphosphoric acid, poly(vinyl fluoride)-metaphosphoric acid, polyethylene glycolmetaphosphoric acid, poly(vinyl alcohol)-sulfuric acid, poly(vinyl fluoride)-sulfuric acid, cellulose acetate-sulfuric acid, polyethylene glycol-sulfuric acid, etc.

It is to be understood that the aforementioned list of polymer blends is only representative of the class of polymer blended membranes which may be prepared and that the invention is not necessarily limited thereto.

It will be helpful in gaining an understanding of the invention to examine initial proof of principle experimentation. The information presented in regard to this experimentation is not meant to limit the scope of the invention in any way.

Several samples of a novel polymer blend membrane were prepared by dissolving 0.25 gram of poly(vinyl alcohol) and 0.1 ml of 14.7M orthophosphoric acid in boiling deionized water, the amount of organic polymer and acid being sufficient to impart a 63/37 weight percent ratio to the resulting polymer blend membrane. The molecular weight of the PVA was 76,000. Commercially available PVA of molecular weight 3,000 or 133,000 could have been used, as it was in preparing other samples. The solution was then poured into an evaporation dish and the water was allowed to evaporate for a period of 18 hours. The resulting film was transparent and possessed a thickness of 30 microns.

A thin film membrane was cut into a disc having a 1" diameter to form membrane 1 of FIG. 1 and platinum was sputter-deposited onto both sides of the disc. The deposited platinum discs each had a thickness of about 400 Angstroms and a diameter of about 1 cm. Deposition was accomplished by means of a Hummer II sputter deposition system supplied by Technics Co. A biased screen between the target and film was used to reduce the electron flux to the membrane. There are many alternative methods which could have been used to form the platinum deposits, such as thermal evaporation or deposition by means of an ink. The porous structure of sputter-deposited catalytic agent is helpful in facilitating spillover of hydrogen ions onto the membrane, but it is not required.

Referring to FIG. 1, membrane 1 was mounted in test fixture 2, which may also be referred to as a sample cell, membrane housing, or test sensor. The above mentioned platinum deposits 5 served as catalytic agent to promote dissociation and reassociation of hydrogen. Electrical contact was made to the platinum through copper platens 6, which were held in place by springs (not shown) extending between the platens and interior surfaces of the sample cell. Platens 6 did not cover the entire surface of the catalytic agent, through FIG. 1 shows this to be the case. Note that when the catalytic agent is electrically conductive and not discontinuous, electrical contact need be made only at one point. Wire leads 3 and 4 extended from the platens out of the test fixture through means for sealing against gas leakage (not shown). Leads 3 and 4 were connected to EMF and current detection means (not shown). Membrane 1 was sealed into test fixture 2 by O-rings 7 so that there were no gas leakage paths between test gas chamber 8 and reference gas chamber 9. Tubing (not shown) was connected at the gas inlets as denoted by arrows 10 and 11 to provide gas flow into chambers 8 and 9 and was also connected to the gas outlets as denoted by arrows 12 and 13 to conduct gas away from the chambers. Gas cylinders and gas mixing and flow control apparatus (not shown) were used to provide gas to test the sensor of fixture 2 in accordance with the herein described experiments. Several cylinders of hydrogen/nitrogen gas mixtures were purchased; an analysis of the contents was supplied with each cylinder. In some experiments, gas was passed through the sensor directly from a cylinder and in other cases a blend was prepared from analyzed cylinder gas and pure nitrogen using the gas mixing apparatus. It must be noted that the gas mixing apparatus was capable of accuracy suitable for proof of principle experimentation but not for more rigorous work. Also, no attempt was made to separately analyze the gas mixtures prepared by diluting purchased gas using said gas mixing apparatus.

Gas flows were established through the chambers of the sample cell with both chamber pressures at about one atmosphere, since the chambers were vented directly to atmosphere. One flow was pure hydrogen (hydrogen partial pressure of approximately 1.0 atm.) and the other was alternated between pure hydrogen and about a 10% by volume mixture of hydrogen in nitrogen (hydrogen partial pressure of approximately 0.1 atm.). The voltage across wires 3 and 4 was recorded by means of a standard laboratory strip chart recorder. The voltage versus time plot was a substantially perfect square wave form. Voltage varied consistently between 0.0 millivolts and negative 29.2 mv. Response was Nernstian; the calculated voltage is also 29.2 mv (at a room temperature of about 22° C.). Note that this is open circuit voltage.

When an ammeter was connected to wires 3 and 4, the measured current was about $3 \times 10^{-3}$ ma. This corresponds to a current density of about $3 \times 10^{-3}$ ma/cm$^2$ and a hydrogen flux of $4.1 \times 10^{-5}$ ft$^3$/ft$^2$—hr; both figures being based on the area of the membrane covered by platinum. The resistance of the membrane was measured when 100% hydrogen was flowing through both chambers of the sample cell. It was about $10^4$ ohms for a 30 micron thick membrane with 1 cm$^2$ of platinum on each surface. This applies to a totally dry membrane. When a membrane which had dried for only 18 hours, as mentioned above, was placed under test, the initial resistance was lower. The increase in resistance is due to removal of the water used in the casting process during initial operation of a sensor.

The resistance, amperage, and voltage of a single membrane were monitored over approximately 100 days of continuous testing. Deviation of voltage from the theoretically expected value was always less than 1%. In these tests, the accuracy of the sensor is felt to be limited by the equipment used.

In another series of tests at a slightly different temperature, the following representative data was collected. A sample gas containing hydrogen from analyzed cylinders was passed through a sensor, as above, the voltage generated was recorded, and a concentration of hydrogen, expressed as partial pressure, was determined from the EMF, using the Nernst equation. Partial pressures are expressed in atmospheres and EMF in millivolts.

| mv | P.P. Sensor | P.P. Analysis |
|---|---|---|
| 1.46 | 0.892 | 0.8973 |
| 28.7 | 0.104 | 0.1034 |
| 57.4 | 0.0107 | 0.0109 |

In addition to platinum, palladium was deposited on membranes for use as catalytic agent. Nernstain voltage response was observed when palladium was used and the strip chart record was indistinguishable from that generated when platinum was used. Other catalytic agents are available and known to those skilled in the art. The catalytic agent need not be electrically conductive; however, then the means for forming electrical connection must be in contact with the catalytic agent over a broad area, to facilitate movement of electrons from sites of the catalytic agent to the electrically conductive substance, or electrode. Areas of membrane which are not adjacent to catalytic agent are not effective in the invention. Hydrogen ions spill over from the catalytic agent to the membrane and then the protons move through the membrane.

Response time of a sensor was tested. When the 100% hydrogen and 10% hydrogen gas streams were alternated as described above, the time required for the voltage to change between steady state values was approximately 6 seconds. It should be noted that the sample cell used is not necessarily designed for quick response.

Sensors were exposed to potential poisons for short periods of time. The presence of carbon monoxide in amounts greater than 0.1% by volume in a hydrogen sample gas stream with a 100% hydrogen reference gas stream caused a change in EMF indicative of a large reduction in hydrogen partial pressure. This apparent drop in hydrogen concentration was much larger than the expected drop due to the effect of dilution of sample gas with CO. This is likely due to the competition by CO with molecular hydrogen for adsorption sites on platinum and palladium. The invention cannot be used to measure the amount of hydrogen, or other gas, present in a sample gas which also contains CO, or other substances which interfere in the same manner, unless the amount of CO, or other substance, is known by other means of constant. The other potential poisons did not interfere with hydrogen concentration measurements. However, a longer term test with hydrogen sulfide caused a change in measured current, though not in voltage.

The above description of the invention has dealt with hydrogen detection. It is clear that any substance capable of dissociating in the presence of a catalyst to yield hydrogen ions may be detected in the same manner. An example is hydrogen chloride (using palladium or nickel catalyst if HCl is at room temperature). The Nernst equation applies in a manner similar to that described herein. The invention is also useful in detecting any gaseous component of a gas sample which is capable of combining with hydrogen ions. Oxygen may be used to illustrate this embodiment. Protons passing through the membrane from a reference gas chamber containing pure hydrogen will combine with oxygen in a sample gas and electrons from the external circuit (for example, wires 3 and 4 of FIG. 1) to form water, in contrast to a hydrogen detector, wherein hydrogen is formed. The Nernst equation is applicable; the Eo term is not 0, as it is when the same substance is present on both sides of the membrane, and the partial pressure of oxygen to the one-half power times the partial pressure of hydrogen divided into the partial pressure of water replaces the analogous term of the equation. Hydrocarbons capable of hydrogenation or dehydrogenation may be subjects of detection. Examples are cyclopentadiene, benzene, isoprene, cyclohexane, and isoamylene.

It is often desirable to avoid the use of a reference gas in the methods and apparatus of detection described herein. This may be accomplished by using a reference substance in the form of a solid. As discussed herein, it is necessary that a substance with a known partial pressure of hydrogen be used as a reference. It is also necessary that the reference partial pressure remains substantially constant as hydrogen is added to or removed from the reference substance.

Figure 3:
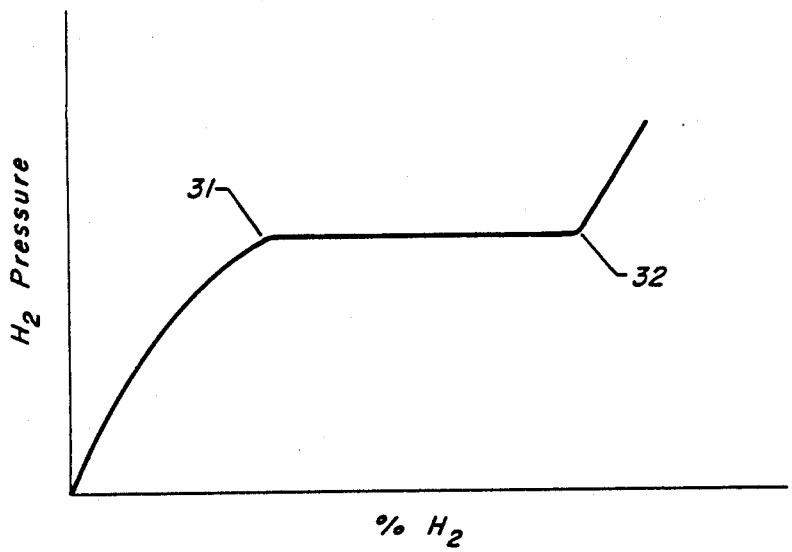
FIG. 3 is a portion of a phase diagram of a solid reference substance capable of use in an embodiment of the present invention, in which hydrogen partial pressure of the substance is plotted against the amount of hydrogen in the substance. If the plot were extended to larger amounts of hydrogen, several plateaus might appear.

In the sensor of the present invention, the EMF developed is an open circuit value. Thus, theoretically there are no electrons flowing in the external circuit to combine with protons passing through the membrane and therefore no change in reference hydrogen concentration. Of course, in actuality there is a small current flowing and reference hydrogen concentration is constantly changing. A reference substance must possess the characteristic of constant hydrogen partial pressure while hydrogen concentration changes. FIG. 3 depicts a portion of a phase diagram of a solid substance suitable for use as a reference substance in the present invention. For a sensor having a solid reference substance to function properly, the hydrogen concentration must lie on the plateau, or horizontal portion, of the curve of FIG. 3, the plateau lying between points 31 and 32. As the hydrogen content of the reference substance increases or decreases due to operation of the sensor, that is, as hydrogen, or other substance, forms from the protons which pass through the membrane and the electrons which flow in the external circuit, the point representing the reference substance moves along the plateau. However, as long as the point is on the plateau the hydrogen partial pressure remains constant and, therefore, the reference substance is useful. It can be seen that a particular reference substance has a limited life. Since the time required to change the hydrogen concentration beyond the limits represented by points 31 and 32 can easily be measured in months or years, the use of a solid reference is practical. Since the flow of protons through the membrane may be in either direction, hydrogen content of the solid reference substance may increase or decrease. When it passes above point 32 or below point 31, the reference substance must be replaced.

Metal hydrides are, in general, suitable for use as solid reference substances in this invention, since their phase diagrams are usually similar to that of FIG. 3. There may be several plateaus on one diagram, so that there is a choice of reference partial pressures while using one particular substance. Examples of metal hydrides include substances consisting of hydrogen and oxygen with tungsten, molybdenum, vanadium, or iridium, hydrogen-zirconium-nickel compounds, hydrogen-zirconium-platinum compounds, and compounds of hydrogen with platinum, palladium, zirconium, hafnium and/or vanadium. Further examples comprise compounds of hydrogen and elements of atomic numbers of 3, 11, 12, 19 through 28, 37 through 48, 55 through 60, 62, 64, 72 through 78, 90, and 92.

Figure 2:
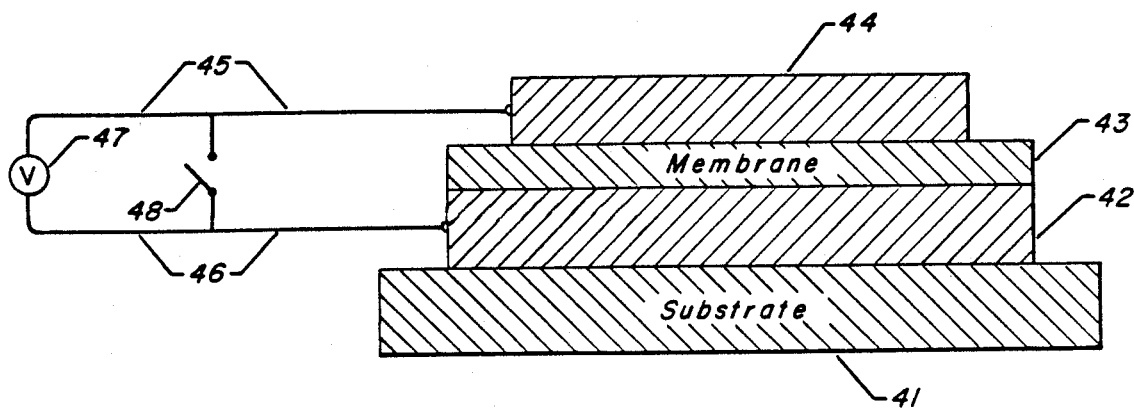
FIG. 2 is a schematic representation, in cross-section, of the test sensor used in initial proof of principle experimentation for the embodiment which utilizes a solid reference substance. It is not to scale.

In proof of principle experimentation, the apparatus of FIG. 2 was fabricated. Palladium layer 42 of approximately 5000 angstroms thickness was sputter-deposited on substrate 41. The substrate used was alumina. Choices of substrate may be made from a wide variety of materials and are not a part of the invention. The palladium layer was moistened with DI water and a 63/37 PVA/$H_3PO_4$ membrane 43 was cast over it in the same manner as described above. The membrane had a thickness of approximately 40 microns. Platinum layer 44 was sputter-deposited on membrane 43 to a thickness of approximately 400 angstroms. Wires 45 and 46 were attached to platinum layer 44 and palladium layer 42. The wires were connected to voltmeter 47. In addition, switch 48 was provided in parallel with the voltmeter to complete an external circuit when desired.

The apparatus was exposed to hydrogen gas for about two hours, with switch 48 closed, to add hydrogen to palladium layer 42 to provide the reference substance. Hydrogen dissociated at platinum layer 44 and the protons passed through membrane 43 while the electrons from the dissociated molecules flowed through the external circuit consisting of wires 45 and 46 and switch 48. It is not necessary to form the reference substance in place in this manner; palladium hydride could have been deposited on the substrate. The palladium hydride served as both catalytic agent and reference substance.

The apparatus depicted in FIG. 2 is an example of a sample cell or membrane housing. The space adjacent to catalytic agent 44 comprises the sample gas chamber. The space occupied by reference substance 42 comprises the reference chamber. Membrane 43 comprises a substantially imporous partition separating the chambers. If it were desired to use a catalytic agent separate from the reference substance, catalytic agent would be depicted as a layer between the layers 42 and 43.

After completion of fabrication of the sensor, hydrogen gas at various concentrations was passed over the sensor. This was accomplished by passing gas through tubing inserted under the lip of an upside-down beaker placed over the sensor while it was resting on a lab bench. Switch 48 was open, since it is used only during fabrication of the sensor, i.e., during hydrogenation of the palladium. EMF obtained (from voltmeter 47) was converted to sensed concentrations of hydrogen expressed as partial pressure. Following are the sensor values at each analysis value, both expressed in atmospheres. The analyses provided by the gas supplier and the analyses calculated after dilution are expressed as partial pressures. The last three mixtures in the table were prepared by dilution of purchased gas.

| P.P. Sensor | P.P. Analysis |
| --- | --- |
| 1 | 1 |
| 0.1 | 0.1 |
| $1.03 \times 10^{-3}$ | $9.9 \times 10^{-4}$ |
| $2.05 \times 10^{-4}$ | $2.07 \times 10^{-4}$ |
| $1.27 \times 10^{-4}$ | $1.3 \times 10^{-4}$ |
| $9.3 \times 10^{-5}$ | $8.7 \times 10^{-5}$ |

The lack of exact agreement of the values is thought to result from the relatively crude gas mixing equipment and experimental procedures and it is expected that better agreement with the theoretical would result from more sophisticated experimentation. Further, as mentioned herein, exact agreement is not required of a commercial sensor.

The reference partial pressure of hydrogen which is used in the Nernst equation to determine EMF is easily calculated. For example, niobium hydride has a hydrogen partial pressure of approximately $10^{-6}$ atmospheres, as calculated by the relationship below. Note that in the plateau region of the phase diagram, niobium, hydride and certain other hydrides exist in three phases, two condensed and one gaseous (molecular hydrogen).

$$\tfrac{1}{2} \ln P = (A/RT) - (B/R),$$

where A=enthalpy difference between the two hydride phases expressed in kcal/gm-atom, B=entropy difference between the two hydride phases expressed in cal/gm-atom-°K, $P = P_2$ or $P_1$ as defined above, and R and T are as defined above.

Figure 4:
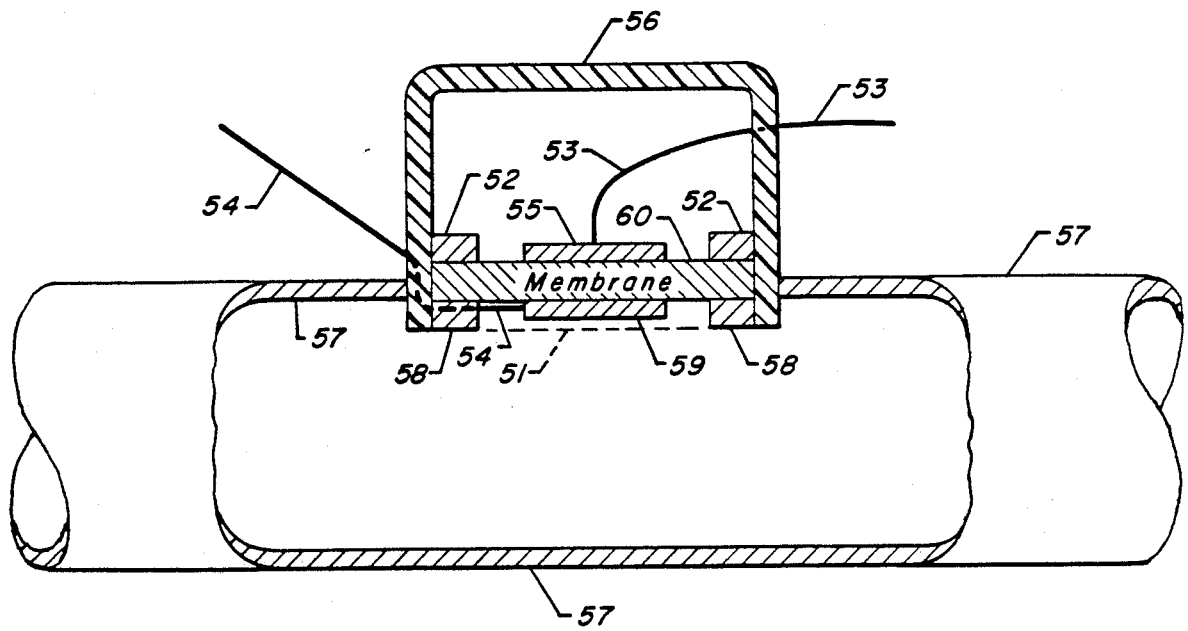
FIG. 4 depicts, in a sectional view, a sensor with a sealed reference chamber mounted on a pipeline. It is not to scale and has non-essential elements omitted.

It can be seen that a membrane mounted in a cell such as depicted in FIGS. 1 and 4 may be subjected to high differential pressures which may deform or burst the membrane. A composite membrane may be fabricated by casting a solution prepared as described above on a flexible porous support. A supported membrane assembly may be fabricated by attaching a membrane which is cast and dried as above to a rigid porous support. In the case of a PVA/H$_3$PO$_4$ membrane, attachment is accomplished by moistening the surface of the membrane and support and pressing the moistened surface together. The moisture will evaporate.

It is contemplated that any porous substrate which possesses a structural strength greater than the thin film membrane may be employed. Some examples of these porous supports will include substances such as glass cloth, polysulfone, cellulose acetate, polyamides, ceramics such as alumina, glass, porcelain, etc. which have been fabricated to possess the necessary porosity, etc. The amount of blend which is cast upon the flexible porous support will be that which is sufficient to form a thin film membrane having a thickness within the range herein set forth. After casting, the mutually miscible solvent such as water is removed by conventional means such as normal evaporation or forced evaporation by the application of external heat, application of vacuum, etc., and the desired membrane comprising the thin film blend composited on the porous support may be recovered and utilized in an appropriate gas sensor apparatus.

A polymer blend was prepared by dissolving 0.5 gram of 16,000 molecular weight poly(vinyl alcohol) and 0.2 ml of orthophosphoric acid in boiling deionized water, the amount of organic polymer and acid being sufficient to impart a 63/37 wt. % ratio to the resulting polymer blend. After a period of time sufficient to form the blend had passed, the solution was stirred and poured onto the top of a fine glass cloth which was positioned in a standard Petri dish. The water was allowed to evaporate for a period of 48 hours and the resulting membrane composite comprising a thin film membrane composited on, or with, the glass cloth having a thickness of 95 microns was recovered.

In like manner, a polymer blend membrane was prepared by dissolving 0.17 cc of sulfuric acid and 0.5 gram of 16,000 molecular weight poly(vinyl alcohol) in boiling deionized water. After a period of time during which a blend had formed, the solution was poured onto the top of a fine glass cloth positioned in a standard Petri dish. The water was allowed to evaporate during a period of 48 hours and the resulting membrane composite was recovered.

The PVA/H$_3$PO$_4$ composite membrane was cut into a circle having a 1" diameter and platinum electrodes $\tfrac{1}{2}$" in diameter were sputter-dispersed on each side of the membrane. The membrane was then placed in a sample housing similar to that of FIG. 1. A reference gas consisting of 100% hydrogen and a sample gas comprising 90.013% nitrogen and 9.987% hydrogen were each passed through the two chambers. An EMF of 29.6 mv was measured; this compares to a calculated voltage of 29.5 millivolts at a temperature of 25.3° C. In addition, it was found that the resistivity was $0.375 \times 10^5$ ohm-cm. In a similar manner, the PVA/H$_2$SO$_4$ membrane was tested and the sensor voltage was found to be the same as that when the membrane comprising a blend of poly(- vinyl alcohol) and orthophosphoric acid was used. However, the resistivity was higher.

As an illustration of the greater structural strength of the polymer blend composited on a porous solid support as exemplified by the blends of the present invention when compared to unsupported membranes, two polymer blend membranes were prepared. The polymer blend was prepared by dissolving 0.5 gram of poly(vinyl alcohol) having a molecular weight of 16,000 and 0.2 ml of orthophosphoric acid in boiling deionized water. The resulting blend was cast onto a glass cloth having a thickness of 30 microns. A second blend was prepared by admixing like proportions of poly(vinyl alcohol) and orthophosphoric acid and casting the resulting blend onto a Petri dish without a support. After removal of the solvent, the two membranes were recovered.

Each membrane was placed in a holder which enabled air pressure to be exerted against one side of the membrane while the other side was at atmospheric pressure. When exposed to 5 psig, the unsupported membrane burst at its center in less than 1 minute. At 2 psig another sample of unsupported membrane bulged and was permanently deformed. The composite membrane was subjected to various pressure levels in 5 psig increments with one minute hold time between increases in pressure. It burst at 35 psig, shearing at the edges of the test hole in the holder. The point of failure leads one to believe that holder design caused the shearing and that a higher burst pressure would be observed in a different holder.

A poly(vinyl pyrrolidone)/orthophosphoric acid membrane composited on a fine glass cloth was prepared. The composition was 45 mole percent polymer and 55 mole percent acid. With pure hydrogen and 10% hydrogen flowing, the EMF was 29.1 mv. Current after 24 hours was 0.0076 ma and resistivity was $7.4 \times 10^5$ ohm-cm.

A poly(ethyloxazoline)/orthophosphoric acid membrane composited on a fine glass was prepared. The composition was 50/50, expressed as mole percent. EMF was 29.2 mv with a 10:1 gas ratio. Current was 0.0026 ma and resistivity was $5.2 \times 10^5$ ohm-cm.

As is common in many analysis instruments, the sample gas provided to a sensor may require conditioning in order to achieve effective detection. Of course, any particulate matter and liquid droplets are removed. The extent of conditioning depends on the particular gas involved and its state. For example, an extremely hot gas must be cooled to a sufficiently low temperature so as not to degrade the apparatus by melting sensor components, including the membrane. A relatively cold gas may need to be heated to a temperature which promotes a reasonable response time of the apparatus. A related factor to be considered is the necessity for knowing the temperature for use in the Nernst equation. The temperature may be measured or the temperature may be maintained at a pre-established constant value. If the calibration gas temperature is maintained at the same value, the matter is simplified. Water vapor and/or other substances are often removed from or added to a sample gas stream. Other sample-conditioning techniques may be required. For example, in a situation where the concentration of the unknown substance is extremely large and capable of saturating the apparatus, the sample may be diluted by addition of a known amount of inert gas. The actual concentration of undiluted sample can then easily be calculated.

a detector may take many forms. A portable battery-operated unit may be used as a "sniffer" to detect the presence in the atmosphere of a particular gas due to leakage from a closed system. A detector may be permanently mounted in a particular location to detect leaks. When conditioning is not required, a detector may be fabricated for insertion directly into a process pipeline. When a gas sample must be conditioned, a small sidestream may be withdrawn from a process pipeline on a continuous or intermittent basis and passed through a sample gas chamber. A quantity of reference gas may be sealed into a reference gas chamber instead of providing a continuous flow.

Figure 5:
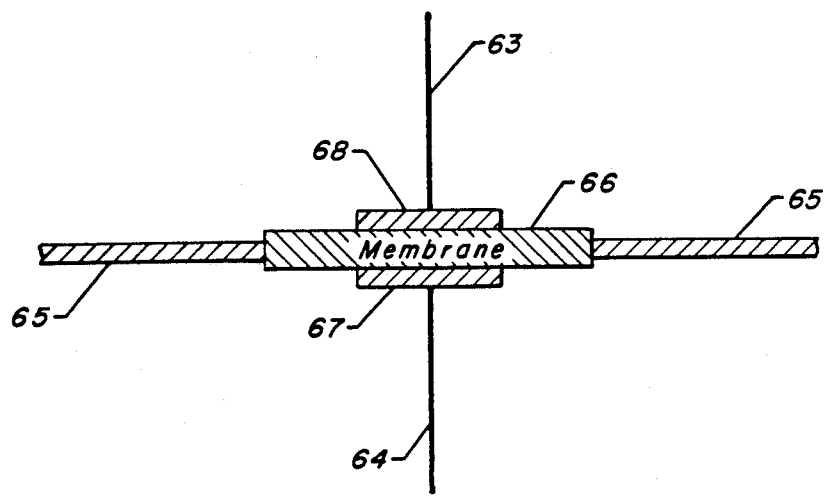
FIG. 5 depicts an embodiment of the inventiion, in a sectional view, in which a membrane is part of a partition separating a sample gas chamber from a reference chamber.

As used herein, the term "detection" includes not only sensing presence or absence of the detected substance, but measurement of the amount of substance present, either in order of magnitude or exact amounts. Gas sample refers to any portion of a gas which is the subject of detection. A gas sample may have only one component. Sample cell or membrane housing or test fixture refers to a housing or fixture which holds an electrolyte element and other required components. FIG. 5 depicts a membrane housing. Sensor is a general term denoting sensing apparatus, such apparatus comprising a membrane housing. Membrane or electrolyte element refers to an ion-conducting substance suitable for use as an electrolyte in the concentration cell of this invention which has been formed into a particular physical entity, either with or without additional substances, for use in the invention. Where an electrolyte element surface is referred to as in common with a gas or gas chamber, the meaning is the same as exposed to a gas or gas chamber and such reference does not preclude the presence of catalytic agent and electrodes at or covering the surface. Gas may diffuse through covering material. Sample gas chamber refers to any space in which gas which is the subject of detection exists. For example, a sample cell can form a part of a pipeline such that the gas flowing in the pipeline is the sample gas and the pipeline is the sample gas chamber. The term "gas" is used herein to include vaporized liquids regardless of boiling point characteristics of the substance. As used herein, miscible means capable of being mixed where there may only be a very small degree of solubility. As is familier to those skilled in the art, the terms concentration and partial pressure are often used interchangeably; partial pressure expresses concentration. Compatible may be taken to mean that compatible compounds will form the polymer-blend composition of matter.

The design of sample cells, or detectors, or membrane housings, is well known. Many configurations are possible; FIG. 1 provides an example of one type. FIG. 4 depicts an embodiment of the invention where membrane housing 56 is mounted (attachment means not shown) in the wall of pipeline 57. Gas is present and may or may not be flowing in the pipeline. The sample gas chamber is the interior of the pipe adjacent to housing 56, while the reference chamber is defined by housing 56 and solid electrolyte membrane 60. Reference gas is sealed into the reference gas chamber; thus it is necessary to replace the reference gas at intervals upon its changing in concentration as a result of the cell reaction sufficiently to affect sensor results. It should also be noted that the membrane is not expected to be totally impermeable and that substances in addition to hydrogen ion may pass through it. Permeability experimentation has not been accomplished, except to the extent indicated herein. Alternatively, the reference chamber may contain a solid reference substance. Electrically conductive catalytic agent is present on both sides of membrane 60, as shown by reference numbers 55 and 59. Wire leads 53 and 54 extend outside the apparatus for connection to voltage detection means. Retaining rings 52 and 58 serve to hold membrane 60 in place at its perimeter (exact detail not shown). Screen 51 is provided to protect membrane 60 from the impact of large particles or objects. If a greater membrane surface area than that of FIG. 4 is desired, a detector may be fabricated in the form of a cylindrical probe for insertion into a pipeline. Membrane material may be placed over a perforated pipe which is sealed at one end. The interior of the perforated pipe is the reference gas chamber. It may be desirable to protect the membrane and catalytic agent by covering it with a porous substance through which sample gas can pass.

Referring to FIG. 5, an embodiment of the invention in which a membrane 66 serves as a part of partition 65 is shown. Partition 65 separates a sample gas chamber from a reference gas chamber. Catalytic agent 67 and 68 and wire leads 63 and 64 perform the functions discussed above.

We claim as out invention:

1. Apparatus for detection, in a gas sample, of a gaseous component which is capable, in the presence of a catalytic agent, of dissociating to yield hydrogen ions or of combining with hydrogen ions comprising:
    (a) a thin film polymer blend macroscopically homogeneous membrane possessing a high protonic conductivity and which is formed by evaporating the solvent from a solution of a phosphoric acid and an organic polymer, wherein said phosphoric acid is present in the blend in an amount in the range of about 10% to about 70% by weight of the blend and is selected from a group consisting of hypophosphoric acid, metaphosphoric acid, orthophosphoric acid, pyrophosphoric acid, and polyphosphoric acid, and wherein said organic polymer is present in the blend in an amount in the range of about 90% to about 30% by weight of the blend and is selected from a group consisting of poly(vinyl alcohol), poly(vinyl fluoride), polyethylenimine, poly(ethylene glycol), cellulose acetate, poly(ethoxyoxazoline), poly(vinyl sulfonic acid), poly(vinyl pyridine), poly(vinyl pyrrolidone), polyimide, poly(acrylamide), poly(acrylic acid), poly(N-isopropyl acrylamide), poly(N,N-dimethyl acrylamide), and copolymers having as repeat units the monomer units used in the polymers of said group;
    (b) a membrane housing comprising a sample gas chamber and a reference substance chamber separated by a partition comprising said membrane, said membrane having a first surface in common with the sample gas chamber and a second surface in common with the reference substance chamber;
    (c) two separate portions of catalytic agent effective to promote dissociation and combination, a first portion in contact with said first surface and a second portion in contact with said second surface of said membrane;
    (d) means for forming electrical connection in operative contact with said catalytic agent at said first surface and with said catalytic agent as said second surface; and
    (e) means for measuring EMF between said means for forming electrical connection, the existence of said EMF being indicative of the presence of said gaseous component in said gas sample and the magnitude of said EMF being proportional to the concentration of said gaseous component in said gas sample.

2. The apparatus of claim 1 further characterized in that said catalytic agent comprises a substance selected from a group consisting of platinum, palladium, and alloys thereof.

3. The apparatus of claim 1 further characterized in that said catalytic agent is electrically conductive.

4. The apparatus of claim 1 further characterized in that said catalytic agent is porous to said gaseous component.

5. The apparatus of claim 1 further comprising means to supply sample gas to said sample gas chamber and reference gas to said reference substance chamber.

6. The apparatus of claim 1 further including means to convert said EMF measurement to concentration.

7. The apparatus as set forth in claim 1 in which said membrane possesses a thickness of from about 0.1 to about 500 microns.

8. The apparatus as set forth in claim 1 in which said polymer is poly(vinyl pyrrolidone) and said acid is orthophosphoric acid.

9. The apparatus as set forth in claim 1 in which said polymer is poly(vinyl alcohol) and said acid is orthophosphoric acid.

10. The apparatus as set forth in claim 1 in which said membrane is composited with a flexible porous support.

11. The apparatus as set forth in claim 10 in which said flexible porous support comprises glass cloth.

12. The apparatus as set forth in claim 1 in which said membrane is attached to a rigid porous support.

13. A method for detection, in a gas sample, of a gaseous component which is capable, in the presence of a catalytic agent, of dissociating to yield hydrogen ions or of combining with hydrogen ions, such method comprising:
    (a) contacting said gas sample with a first surface of a thin film polymer blend macroscopically homogeneous membrane possessing high protonic conductivity, which membrane isolates said gas sample from a reference substance, and which is formed by evaporating the solvent from a solution of a phosphoric acid and an organic polymer, wherein said phosphoric acid is present in the blend in an amount in the range of about 10% to about 70% by weight of the blend and is selected from a group consisting of hypophosphoric acid, metaphosphoric acid, orthophosphoric acid, pyrophosphoric acid, and polyphosphoric acid, and wherein said organic polymer is present in the blend in an amount in the range of about 90% to about 30% by weight of the blend and is selected from a group consisting of poly(vinyl alcohol), poly(vinyl fluoride), polyethylenimine, poly(ethylene glycol), cellulose acetate, poly(ethyloxazoline), poly(vinyl sulfonic acid), poly(vinyl pyridine), poly(vinyl pyrrolidone), polyimide, poly(acrylamide), poly(acrylic acid), poly(N-isopropyl acrylamide), poly(N,N-dimethyl acrylamide), and copolymers having as repeat units the monomer units used in the polymers of said group;
    (b) exposing a second surface of said membrane to a reference substance; and
    (c) detecting EMF between means for forming electrical connection with two separate portions of a catalytic agent effective to promote dissociation and combination, where a first portion of catalytic agent is in contact with said first surface and a second portion of catalytic agent is in contact with said second surface of said membrane, the existence of said EMF being indicative of the presence of said gaseous component in said gas sample and the magnitude of said EMF being proportional to the concentration of said gaseous component in said gas sample.

14. The method of claim 13 further characterized in that said gaseous component is elemental hydrogen.

15. The method of claim 13 further characterized in that said gaseous component is elemental oxygen.

16. The method of claim 13 further characterized in that said reference substance is in gaseous form.

17. The method of claim 13 further characterized in that said reference substance is in the form of a solid, which is in contact with said second catalytic agent portion and exhibits a substantially constant known hydrogen partial pressure during practice of said method for detection.

18. The method of claim 17 further characterized in that said reference substance is a metal hydride.

19. The method of claim 17 further characterized in that a single substance serves as both reference substance and catalytic agent.

20. The method of claim 17 further characterized in that said reference substance and catalytic agent is palladium hydride.

* * * * *